United States Patent [19]
Cammarata

[11] Patent Number: 6,141,888
[45] Date of Patent: Nov. 7, 2000

[54] MONITORING WOOD SAMPLE WEIGHT WITH MECHANICAL FORCE PROPORTIONING

[75] Inventor: Charles V. Cammarata, Parsippany, N.J.

[73] Assignee: Delmhorst Instrument Co., Towaco, N.J.

[21] Appl. No.: 09/264,653

[22] Filed: Mar. 8, 1999

[51] Int. Cl.⁷ .................................................. F26B 21/06
[52] U.S. Cl. .................................. 34/536; 34/89; 34/202
[58] Field of Search ............................. 34/396, 493, 536, 34/541, 557, 565, 89, 191, 202; 73/38, 73

[56] References Cited

U.S. PATENT DOCUMENTS

| | | |
|---|---|---|
| 1,593,890 | 7/1926 | Welch . |
| 3,131,034 | 4/1964 | Marsh . |
| 3,744,144 | 7/1973 | Weis . |
| 4,176,464 | 12/1979 | Randolph . |
| 5,226,241 | 7/1993 | Goodwin . |
| 5,325,604 | 7/1994 | Little . |
| 5,587,933 | 12/1996 | Gross ....................................... 364/558 |
| 5,775,003 | 7/1998 | Goodwin, III . |
| 5,957,773 | 9/1999 | Olmstead et al. ........................... 460/7 |

*Primary Examiner*—Stephen Gravini
*Attorney, Agent, or Firm*—Notaro & Michalos P.C.

[57] ABSTRACT

In a monitoring system for a wood drying kiln having a housing with an interior area for placement of a charge of wood for drying the charge of wood, the interior area having a floor, environment devices for adjusting heat and humidity in the interior area of the kiln, and a control unit for controlling the environment devices, the improvement is a support in the interior area for supporting a representative sample of the charge of wood, a sensor mounted to the support for sensing the weight of the sample which is a function of moisture content in the sample and a proportioning mechanism connected between the sensor and the sample for suspending the sample and for applying a proportioned force resulting from the weight of the sample to the sensor. The sensor is connected to the control unit for generating a signal which is proportional to the weight, and thus, to the moisture content of the sample. A stand on the kiln floor has a member for carrying the support at a location which is spaced from the wood charge without requiring and kiln wall space. The invention also includes the possibility of supporting the sensor from the ceiling and at any location in the kiln whether the sensor is supported from the ceiling or the floor. The invention is also useful in kilns for drying other materials than wood.

11 Claims, 7 Drawing Sheets

MONITORING WOOD SAMPLE WEIGHT WITH MECHANICAL FORCE PROPORTIONING

FIELD AND BACKGROUND OF THE INVENTION

The present invention relates, in general, to kilns for drying wood, and, in particular, to a new and useful wood sample weighing method and apparatus which is used in a system for controlling at least one environmental parameter within the kiln.

It is known that by controlling the environmental conditions within the interior of a kiln, lumber positioned within the kiln may be dried at a controlled rate to minimize drying related defects of the lumber as it is dried. This includes conditions such as temperature, pressure, humidity and the like in steam, dehumidification, vacuum or other kilns.

In order to control the kiln temperature, humidity, or other condition, it was common practice for a sample piece of lumber to be selected from the stack of lumber being dried, and the moisture content of the sample was determined outside the kiln, at preselected intervals of time. With the moisture content information, the kiln temperature and humidity were altered, if necessary, to ensure that the lumber was dried at the desired rate.

The moisture content of the lumber sample was typically determined by this periodic removal of the sample from the kiln and by weighing of the removed sample or measuring some other characteristic of the removed sample to measure the moisture content. Such a process was time-consuming, susceptible to error and likely to effect the environment of the kiln interior since the kiln interior was exposed to ambient conditions during each removal of the sample from the kiln. The process was also uncomfortable and potentially dangerous in that the operator had to enter the hot kiln.

U.S. Pat. No. 1,593,890 to Welch, discloses an apparatus for drying wood which includes a balance beam for weighing a wood sample held in a horizontally extending position and at a non-disclosed location in a wood drying kiln. Nothing is mentioned in the reference on the survivability of the equipment within the corrosive, quickly-moving, hot, moist atmosphere in a kiln.

U.S. Pat. No. 5,325,604 to Little, discloses a system for use in the control of the environmental conditions, e.g. the temperature and humidity, of a kiln, based on a continuous determination of the moisture content in one or more wood samples in the kiln, which both circumvents the need for removing samples from the kiln and avoids the drawbacks of the Welch Patent. In the Little Patent the wood sample is suspended in a fixture adjacent an interior wall in the kiln which also contains the charge or stack of wood being dried. The fixture or sensor unit, contains a sensor in the form of an electronic load cell or strain gauge which measures force by generating an electric signal which is proportional to the force applied to the sensor. The fixture in the Little Patent requires an area of free wall space. U.S. Pat. No. 5,325,604 to Little is incorporated here by reference, in particular for its teaching of the structure and function of a kiln and the environmental control units therefor.

U.S. Pat. No. 5,775,003 to Goodwin, III, discloses a sensor for measuring the weight of a wood sample in a kiln while the sample hangs in a tunnel which partly encloses the sample. The tunnel is suspended on the wood charge in the plenum.

U.S. Pat. No. 5,226,241 to Goodwin, III, U.S. Pat. No. 4,176,464 to Randolph, U.S. Pat. No. 3,744,144 to Weis, and U.S. Pat. No. 3,131,034 to Marsh, disclose other methods and apparatuses for controlling wood drying kilns, including systems which weigh the entire lumber charge to determine its moisture content.

A need remains for further improvements in this field.

The present invention is not limited to the drying of any particular type of lumber or even any particular type of drying kiln but can be used for any kiln of any design and for drying any product.

SUMMARY OF THE INVENTION

An object of the present invention is to provide a method and apparatus for controlling environmental conditions of a kiln within which a stack of lumber is dried, comprising a sensor unit or fixture within the kiln and from which a sample from the stack is suspended. The sensor unit generates a signal corresponding to the weight of the sample and included a force proportioning mechanism for accommodating samples having different ranges of weight. In this way a sensor or strain gauge of only one rating can be used for a wide variety of samples and kilns. The weight of the sample is suspended from the proportioning mechanism and the signal is used to determine the actual moisture content of the sample, continuously as a function of the weight of the sample and the signal generated by the sensor. As with the U.S. Patant to Little, the thus measured moisture content is used as a control variable for altering environmental conditions in the kiln.

Another object of the invention is to provide a stand or base for the sensor unit which is mounted to the floor of the kiln at a spaced location from the wood stack but in the kiln plenum. This eliminates the need for free wall space of the fixture as needed by the Little Patent, and avoids encumbering the wood charge as required by the U.S. Pat. No. 5,775,003 to Goodwin, III.

The placement of the sample sensor is entirely arbitrary according to the present invention and can be anywhere in the free area of the kiln. The present invention also includes variations which hangs the sample from the ceiling with or without proportioning means. The sample sensor can be in the space above the charge to be dried or in the space between the charge and the kiln wall or in the space between charges, e.g. in a track kiln.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

The invention retains all of the advantages of the prior invention in U.S. Pat. No. 5,325,604 to Little, while improving usability by accommodating wood samples beyond the resolution and capacity of the sensor. The invention also allows for support of the fixture in kilns where there is no suitable vertical support surface.

The invention includes a mechanical force proportioning mechanism, incorporated into an appropriate fixture, which generates a resultant force, Fr, proportional to an applied force, Fa, to the mechanism. The fixture may be mounted on any suitable surface such as an interior kiln wall surface, kiln door or any other structural member of the kiln.

The invention also includes, however, a floor stand or base that supports the fixture at a distance above the floor of the kiln, remote from the charge of wood, and remote from the interior wall surface of the kiln. This floor stand or base can be placed anywhere on the floor in the kiln, such as adjacent the lumber charge, the kiln walls or the doors.

The combination of the stand together with the fixture permits the apparatus to be permanently positioned within the plenum area of the kiln for the duration of the drying operation and removed during loading and unloading.

Figure 1:
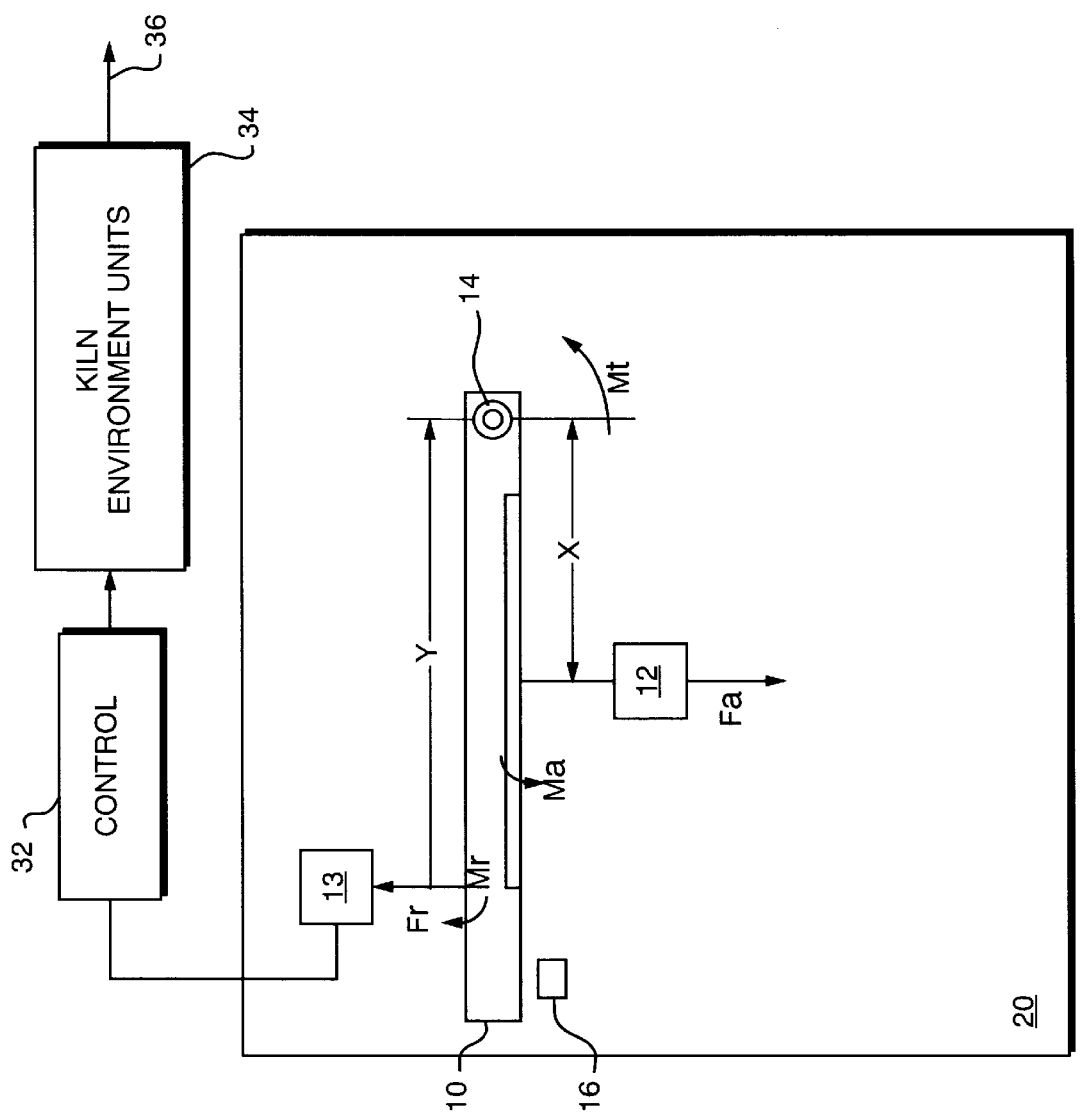
FIG. 1 is a schematic representation of a mechanism of the present invention which helps illustrate some of the principles of the invention.

FIG. 1 illustrates some of the principles of the invention.

Force proportioning is achieved by means of a torque arm 10 supported at one end by a suitable bearing 14 at the torque arm axis, and near the other end by the sensor 13 where the sensor is supported by a fixture plate 20. The sensor 13 measures the force Fr proportionally generated by the force Fa of the wood sample weight 12 and apparatus weight. To avoid possible damage to sensor 13, a fixed stop 16 may be mounted to the support plate 20 below the free end of arm 10. Sensor 13 can be any appropriate sensor for measuring force or weight, such as a strain gauge, a load cell, a spring scale, or any other device for measuring force.

In the calculations below, it is assumed that the dimensional deflection of the senor is much less than the dimensions "x" (between the bearing or journal axis 14 and the sample 12) and "y" (between the bearing and the sensor 13). This essentially creates a fixed geometry. Also, the weight of the apparatus is a known constant and can be removed from the calculations.

The applied force, "Fa", is generated by the weight of the wood sample 12. "Fa" exerted at the distance "X" from the torque arm axis, generates an applied torque, "Ma", about the axis represented by:

$$Ma = Fa * x$$

The resultant force generated an measured by the sensor, "Fr", exerted and measured at the distance "y" from the torque arm axis, generates a resultant torque, "Mr", about the axis represented by:

$$Mr = Fr * y$$

Since the system is static, the total torque about the torque axis, Mt, is zero:

$$Mt = 0$$

and therefore $$Mr = Ma$$

Substituting Mr and Ma yields:

$$Fr * y = Fa * x; \text{ or}$$

$$Fr = Fa * (x/y).$$

From this equation, it is seen that the resultant force is proportioned according to the ratio of the distances of the forces to the torque arm axis.

Figure 2:
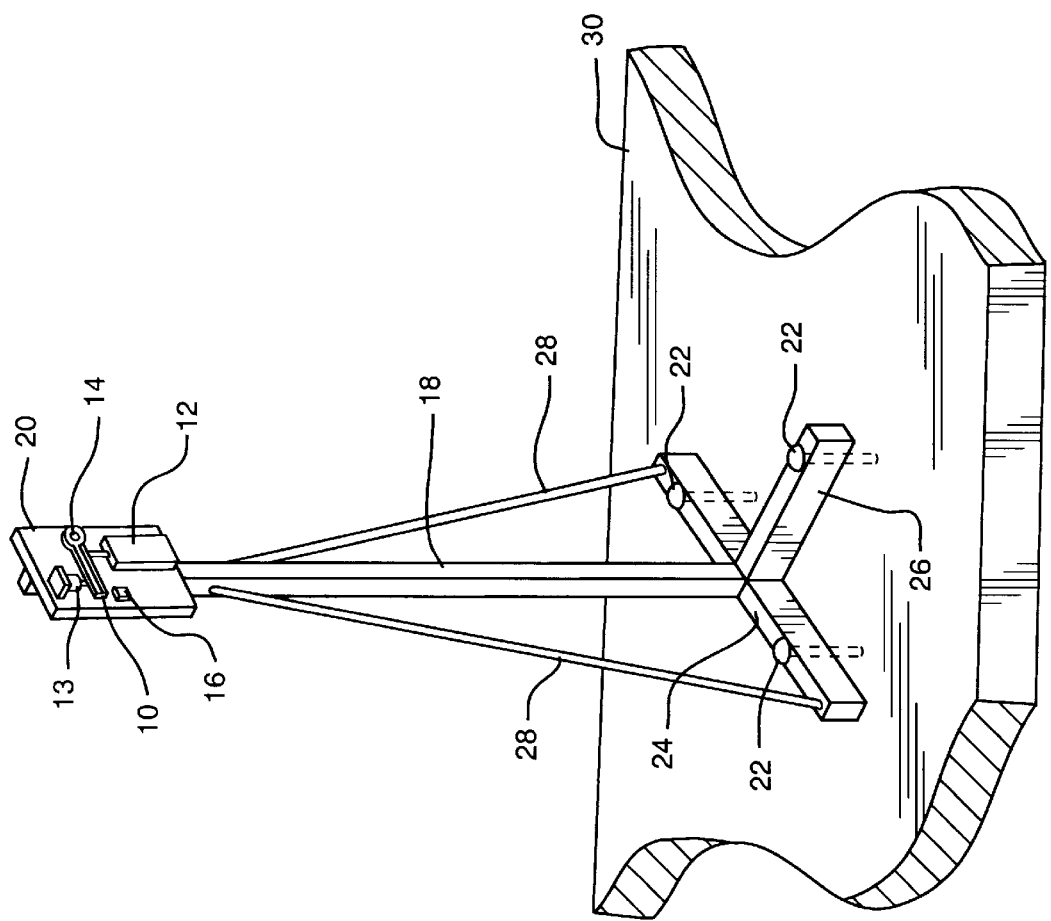
FIG. 2 is a perspective view of the apparatus of the present invention.

In FIG. 2 and throughout the drawings, the same reference numerals are used to designate the same or functionally similar parts of the invention.

As shown in FIG. 2, the vertical support plate or member 20 is mounted at the upper end of a stand formed by a main upright 18, a pair of angled supports 28, a cross leg 24 which is horizontal, and a further leg 26 that forms a stable stand. Pins, bolts, screws or other positioners or fasteners 22 can be used to locate the stand to the kiln floor 30. This provides a vertical support member 20 without requiring any engagement with the stack and also without requiring any free kiln wall space as with the prior art.

As shown in FIG. 1, and in a manner which already disclosed in the prior art, a signal from the senor 13 can be supplied to a control unit 32 for signal processing. A control signal can then be supplied to environment control units such as heaters and humidifiers, shown only schematically at 34, which control the environment in a kiln as shown schematically at 36. Although, FIG. 1 shows strain gauge 13 connected to control 32 by a wire, it is understood that wireless transmission of signals can also be used in accordance with the present invention. For example, telemetry transmission via radio or other signals can be used.

Figure 3:
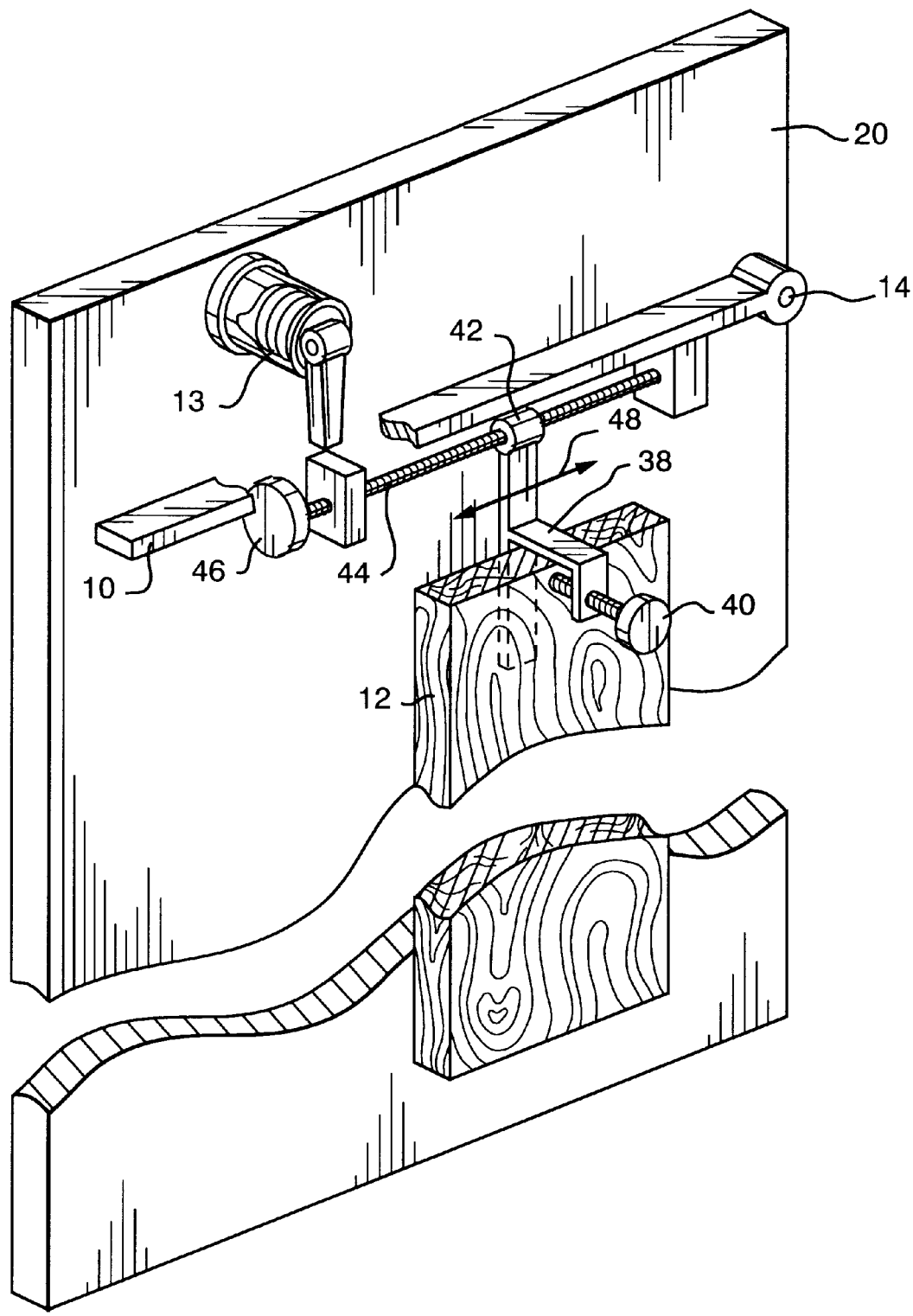
FIG. 3 is a perspective view of a further embodiment of the invention.

In FIG. 3, sample board 12 is shown suspended from a clamp 38. A threaded knob 40 can be used for engaging different samples to the clamp. Clamp 38 is suspended from a threaded bushing 42 which receives a threaded rod 44 that can be turned, for example manually by a knob 46, to change the suspension position of the sample as shown schematically by double arrow 48. This offsets the suspension point from the location on vertical support 20 at which the sensor 13 is mounted, to achieve the proportioning function of the present invention. Any other mechanism which is known to the person having ordinary skill in the art can also be used for adjusting the second position at which the sample 12 is suspended from the first position on support member 20 to which the sensor 13 is fixed.

The invention has discovered that it is not always preferred or possible to limit the weight of the samples due to variations in physical size and type of wood that is to be dried.

Current sensors and support circuitry are limited in capacity and resolution. Senor capacity, "F", is a fixed physical property of the sensor itself. Sensor capacity represents the largest force that can be measured by the sensor. Sensor force resolution, "R", is typically dependent on the sensor and the supporting electronics, and is a fixed fraction of the total capacity of the sensor:

$$R = F/C$$

where C is a constant. Sensor force resolution represents the smallest change in force that can be detected by the sensor.

The prior art determined the weight of the samples by suspending the samples from the sensor mounted on an appropriate fixture, via a clamping mechanism. (See FIG. 2 in U.S. Pat. No. 5,325,604 or FIG. 3 in U.S. Pat. No. 5,775,003 for example). The resultant force exerted on the sensor is equal to the applied force of the weight of the wood sample plus the weight of the clamping mechanism. In this fashion, the weight of the wood sample was limited to the force rating of the sensor in two ways.

1) The weight of the wood sample and clamping mechanism could not exceed the maximum rating of the sensor; and
2) The weight of the wood sample must be of a minimum weight such that the change in wood sample weight representing the necessary rate of change in moisture content of the wood sample for control purposes, a fixed fraction of the total wood sample weight, is greater than the sensor resolution.

The present invention increases the usability of the fixture by allowing for wood samples that would otherwise be beyond the capacity limit or below the resolution limit of given sensor mounted in the fixture.

In the examples below, it is assumed that the dimensional deflection of the sensor is much less than the "x" or "y" dimensions, essentially creating a fixed geometry. Also, the weight of the apparatus is a known constant and can be removed from the calculations.

EXAMPLE 1, CAPACITY

For a given sensor with a specified maximum force capacity of "F" units installed in the prior art (U.S. Pat. Nos. 5,325,604 and 5,775,003) the maximum wood sample weight that can be used can not exceed the equivalent of "F" units of force. In this manner, a wood sample having a weight of:

$$\text{Wood sample weight} = 1.5*F = \text{Applied Force} = \text{Resultant force}$$

could not be measured because the resultant force exceed the capacity rating of the sensor.

With the present invention, the resultant force applied to sensor is manipulated by allowing the end user to vary the "x"/"y" dimensional ratio. If "x" and "y" are positioned such that:

$$x = \tfrac{1}{2}y$$

then $$Fr = Fa*(x/y)$$

$$Fr = Fa*(\tfrac{1}{2}x/y)$$

$$Fr = Fa*(\tfrac{1}{2})$$

In this manner the same wood sample of:

Wood sample weight=1.5*F=Applied force=Fa would have a resultant force:

$$Fr = |1.5|*\tfrac{1}{2}*F = \tfrac{3}{4}*F$$

applied to the sensor in the present invention. The ¾ F value is less than the maximum force F of the sensor, and therefore can be measured.

EXAMPLE 2, RESOLUTION

For a given sensor installed in the prior art with a capacity of "F", a minimum detectable change in force, dF, is defined as:

$$dF = F/R$$

where "R" is a constant.
For the prior art, a wood sample is chosen with:

$$\text{Wood sample weight} = Ws = Fa.$$

The minimum change in wood sample weight representing the necessary change in moisture content of the wood sample for control purposes, "dWs", is a fixed fraction of the total weight of the wood sample:

$$dWs = Ws/Cw$$

where Ws is the wood sample weight and Cw is a constant. Since $$Fa = Ws,$$

$$dFa = dWs$$

In the prior art, $$Fr = Fa,$$

$$dFr = dFa$$

it is known that in order to have effective control:

$$dFr => dF.$$

A wood sample with $$dWs = \tfrac{2}{3}*dF = dFa = dFr$$

would be ineffective in the prior art, since dFr<dF.

With the present invention, the effective minimum force resolution of a sensor is manipulated by allowing the end user to vary the "x"/"y" dimensional ratio. If "x" and "y" are positioned such that:

$$x = 2y$$

then $$Fr = Fa*(x/y)$$

$$Fr = Fa*(2y/y)$$

$$Fr = Fa*2$$

So $$dFr = dFa*2$$

In this manner the same wood sample with:

$$dWs = \tfrac{2}{3}*dF = dFa$$

now has $$dFr = \tfrac{2}{3}*dF*2 = \tfrac{4}{3}*dF$$

which will be effective for control since ⁴⁄₃*dF=>dF.

It has also been learned that it is not always preferred or possible to mount the prior art sensors on the inner walls of the kiln because of differences in kiln structure designs and the possibility of damage that have occurred to the fixtures when lumber is loaded into and unloaded from the kiln.

The present invention permits the fixtures to be placed at any location within the plenum areas of the kiln. Because measured airflow and air speed within the kiln may vary substantially within relatively small distances, the invention also permits optimum placement of the representative samples in areas which most closely reflect the conditions that the layered lumber will experience. Numerous factors can influence the airflow within the kiln such as how the lumber is stacked and the volume of lumber loaded.

Although specific types of kilns and in particular lumber kilns have been mentioned, the present invention can be used with any type of lumber kiln and in fact any type of drying kiln for any product.

Previous techniques required that the capacity of the sensor be selected as a function of the wood sample weight, and vice versa. Major disadvantages were:

1) Limits the end user to a range of sample weights that can be effectively used; and
2) Requires that the manufacturers of the prior art devices purchase and/or stock more than one type of sensor (load cell or strain gauge) in order to accommodate samples beyond the capability of a single sensor type.

Also, previous devices depended on an existing support surface be available in the kiln to support the fixture.

The present invention offers a significant commercial improvement over the prior art by:

1) Allows the end users increased flexibility of wood sample selection to more closely represent their end product by allowing for samples outside the useable capacity restricted by previous inventions.
2) Allows the manufacturer to purchase and stock only one suitable sensor model, allowing the manufacturer the possibility of lower per unit sensor costs, taking advantage of quantity discounts form sensor suppliers.
3) Allows the manufacturer to avoid the problems associated with the availability of sensors of different capacities.
4) Use of the floor stand or base allows usability of the fixture in kilns that would otherwise not, by nature of the design of the kiln, provide a suitable mounting surface for the fixture.

Figure 4:
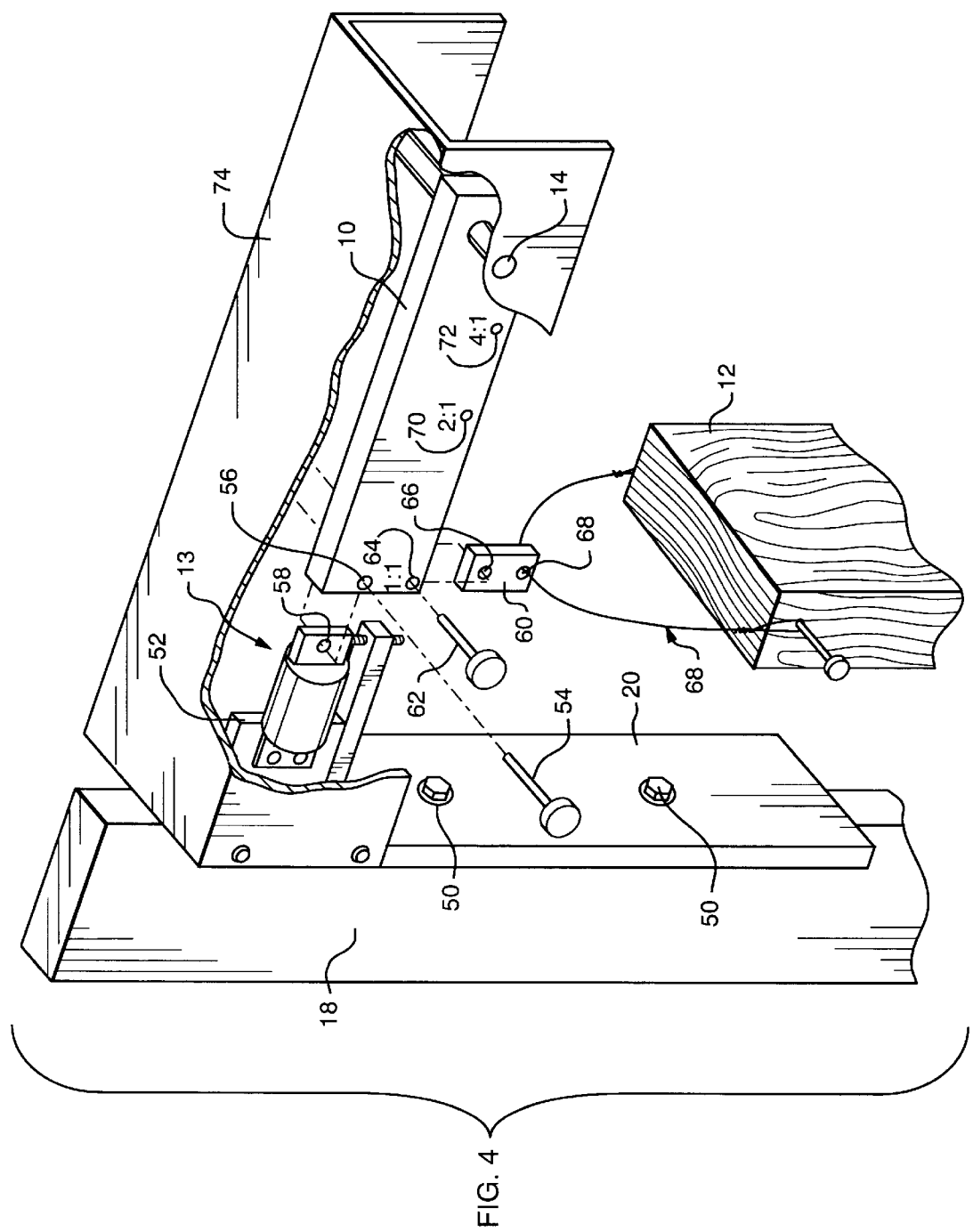
FIG. 4 is an exploded perspective view of a preferred form of the fixture of the present invention.
Figure 5:
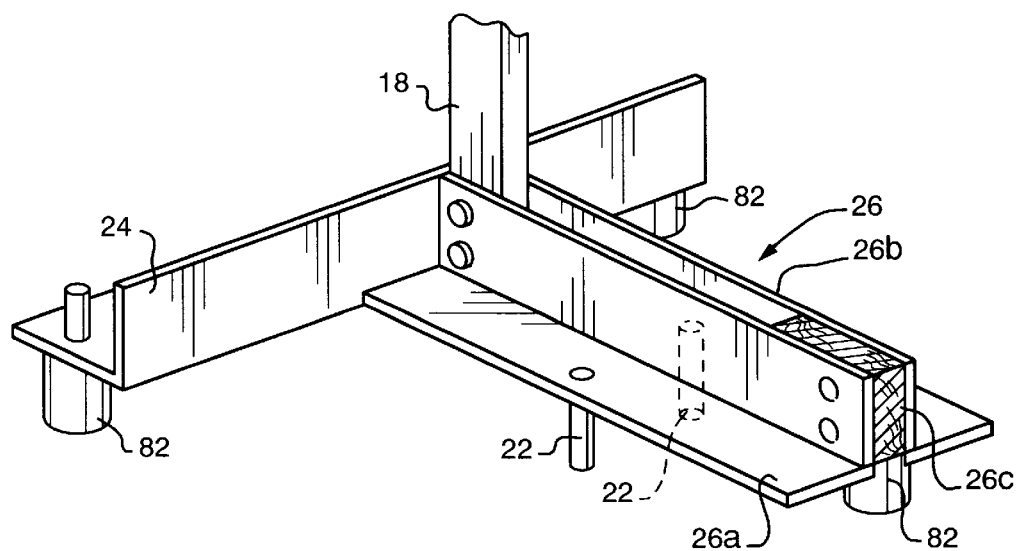
FIG. 5 is a partial perspective view of the lower parts of the stand according to the present invention.
Figure 6:
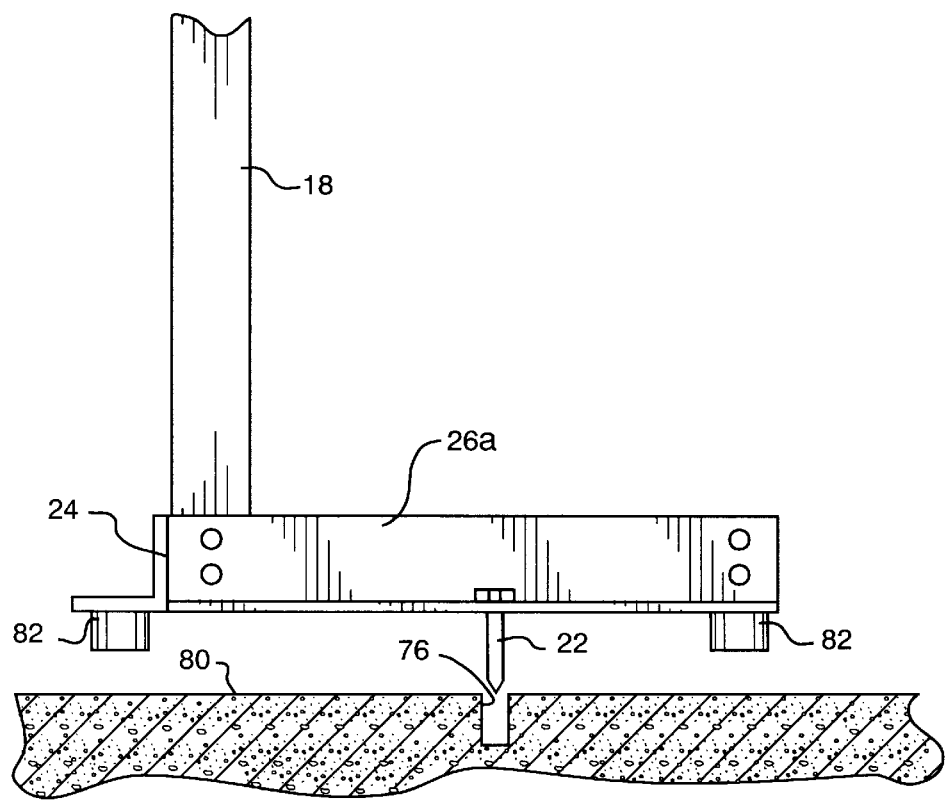
FIG. 6 is a side elevational view of the lower part of the stand and its relationship to kiln floor.

FIGS. 4, 5 and 6 illustrates a preferred embodiment of the invention.

In FIG. 4, support plate 20 which is preferably made of metal, is fastened by a pair of bolts 50 which are threaded into the edge of upright member 18. The sensor or strain gauge 13 has a base fixed to a plate 52 that in turn is fixed to plate 20. The opposite active end of sensor 13 is connected, for example by a removable pin 54 to the arm 10, by aligning holes 56 and 58. A suspension plate 60 is also connected by a second removable pin 62, to arm 10, by aligning holes 64 and 66. A suspension cable 68 having opposite ends connected to the opposite edges of sample 12, is threaded through a further hole 68 in suspension plate 60, to suspend the sample. Additional proportioning holes 70 and 72 are also provided along arm 10, for engaging pin 62 and suspending plate 60, for proportioning the same sensor 13 to carry heavier samples by a factor of 2 and a factor of 4 respectively. Holes 64, 70 and 72 are between the attachment point of arm 10 to sensor 13, and the bearing or journal 14. Bearing 14 extends between the arms of a U-shaped cover or hood member 74 which both covers and protects the arm and sensor arrangement.

In another variation of the invention which uses a support or stand, but no proportioning means, cable 68 can be passed directly through hole 58 at the end of the strain gauge 13 to directly support the sample 12. Although sample 12 is shown suspended from one of its narrow edges, it is understood that the sample can be suspended from its broad edge or even from one of its broad surfaces in a horizontal position. The invention is not limited to any particular orientation for the sample as long as the sensor senses the weight of the sample, either directly or indirectly through the proportioning means.

FIGS. 5 and 6, show details at the lower end of the stand. Upright member 18 is connected to the angle iron forming cross member 24. A pair of angle irons 26a and 26b are bolted together and to upright 18 to form the leg 26. A spacer block 26c spaces the far ends of the angle irons 26a, 26b, by an equal amount. A pair of locator pins 22 each welded to and extending downwardly from the horizontal legs of angle irons 26a, 26b, can be located into a pair of corresponding blind bores 76 drilled into the kiln floor 80. Three rubber feet 82 are fixed to the bottoms of members 24 and 26 for producing a secure and stable, yet vibration resistant support for the stand.

According to the present invention, the base of the stand need not be fixed to the floor but may simply rest on the floor. The weight of the stand and the sensing equipment attached thereto as well as the size of its base, are sufficient to keep the stand upright despite the presence of blowing air in the kiln space. Also, it is understood that some kilns do not have a finished floor of concrete or other material but simply utilizes bare earth or the ground with or without treatment. Accordingly, the term "floor" as used in this application includes both finished and unfinished surfaces at the bottom of a product drying kiln for drying any type of product. Although lumber of various types is dried in the kilns according to the preferred embodiment of the present invention, other products such as hops or other organic or inorganic products can be dried in kilns controlled according to the present invention. This includes various clays, ceramic products, and any other type of product which needs to be dried and which is supplied in charges in the kiln and from which a sample can be selected which is representative of the drying activity in the charge.

According to the present invention, the stand whether supported or attached to the floor, is positioned in a space between the charge and the wall and preferably so that the sensors are held away from the charge and away from the wall. It has been found that placement in fact is not critical and the stand can hold the sample near the wall or near the charge or at any location between these two extremes. In the case of an embodiment of the invention where the sample is suspended from the ceiling, again placement is either between the charge and the wall or over the charge, between the top of the charge and a ceiling in the kiln.

Figure 7:
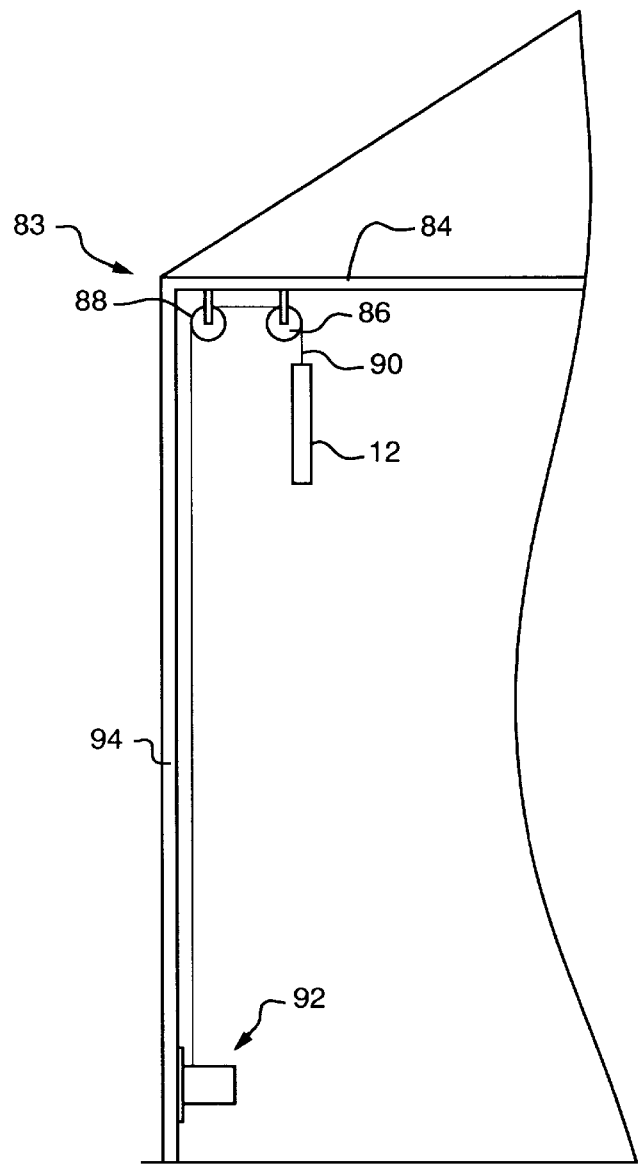
FIG. 7 is a partial schematic side elevational view of a further embodiment of the present invention.
Figure 8:
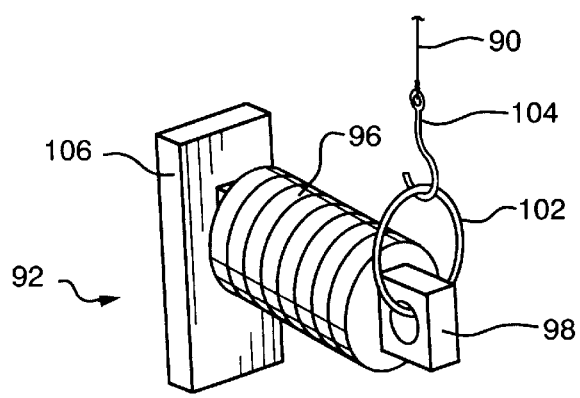
FIG. 8 is an enlarged perspective view of the sensor of the embodiment of FIG. 7.

FIG. 7 illustrates another monitoring system according to the present invention installed in a kiln generally designated 83 having a roof or ceiling 84 from which a pair of pulleys 86 and 88 are suspended for rotation. A sample 12 hangs from one end of a cable 90 and is wrapped over pulley's 86 and 88 and then extends down into a sensor arrangement 92 mounted to a wall or upright 94 of kiln 83. As best shown in FIG. 8, sensor arrangement 92 comprises a load cell, strain gauge or other sensor 96 having an end 98 with a hole for receiving a ring 102. Hook 104 engages ring 102 and is connected to the opposite end of cable 90. With the arrangement of FIG. 7, the upward force applied to the sensor 96 is equal to the downward force and thus the weight of sample 12. A different pulley arrangement can be provided however, as proportioning means according to the present invention.

As shown in FIG. 8, the sensor arrangement 92 includes a wall mounting board 106 which, with pulley's 86 and 88, are the only attachments necessary to the walls or ceiling of the kiln.

Figure 9:
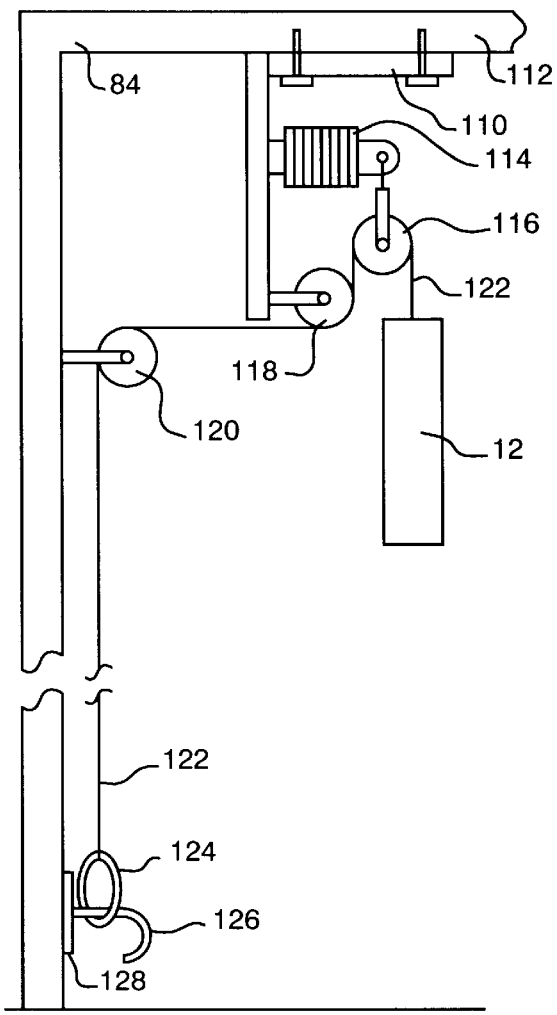
FIG. 9 is a view similar to FIG. 7 of a still further embodiment of the present invention.

FIG. 9 illustrates another embodiment of the invention which utilizes an L-shaped mount 110 connected, for example with bolts, to the girder 112 of a kiln roof 84. A force sensor, such as a load cell or strain gauge 114, has an outer end which suspends a first pulley 116. A second pulley 118 is connected to the upright of mount 110 and a still further pulley 120 is connected to vertical wall or any other vertical support 94 of the kiln. A cable 122 has one end connected to the sample 12. Cable 122 is wrapped over pulley 116, around pulley 118 and around pulley 120 and then extends down wall 94 so that its lower end is connected to a ring 124 engaged onto a hook 126 which can be connected to a plate 128 or directly to the kiln wall 94.

In the embodiment of FIG. 9, proportioning means are provided for the sensor 114 in that the force experienced by the load cell is two times the sample weight, thus increasing resolution.

Figure 10:
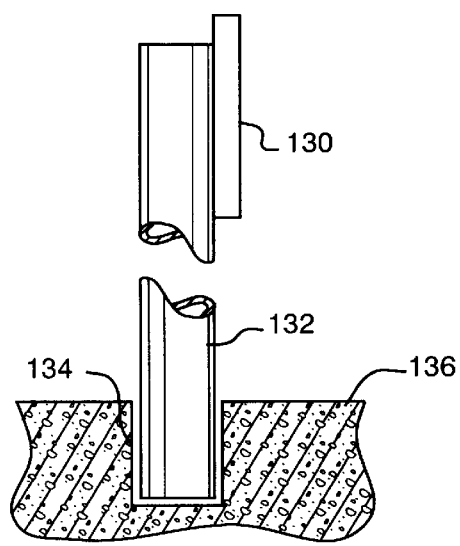
FIG. 10 is a fragmentary elevational view, partly in section, showing a still further embodiment of the present invention.

FIG. 10 illustrates a further embodiment of the invention in which a mounting plate or support 130 is carried by a vertical pole 132 which has a lower end that simply sits in a blind bore 134 in a concrete kiln floor 136. In this way a single leg or pole is used to support the sensor of the present invention and minimum alterations are needed to the interior of the kiln.

While specific embodiments of the invention have been shown and described in detail to illustrate the application of the principles of the invention, it will be understood that the invention may be embodied otherwise without departing from such principles.

What is claimed is:

1. In a monitoring system for a product drying kiln having a housing with an interior area for placement of a charge of product for drying the charge of product, the interior area having a floor, environment means for adjusting at least one environmental condition in the interior area of the kiln, and control means for controlling the environment means, the improvement comprising:

a support spaced from the charge in the interior area for supporting a representative sample of the charge of product, the support comprising a stand having a lower end adapted to be supported on the kiln floor away from the charge, and a vertical support member above the lower end for supporting a sensor; and a load cell, strain gauge or spring scale sensor mounted to the support member for sensing the weight of the sample which is a function of moisture content in the sample, the sensor being operatively connected to the control means for generating a signal which is proportional to the weight, and thus, to the moisture content of the sample.

2. The improvement of claim 1, including proportioning means operatively connected between the sensor and the sample for suspending the sample and for applying a proportioned force resulting from the weight of the sample to the sensor.

3. The improvement of claim 1, wherein the support is structured to suspend the sample with a broad side of the sample extending perpendicular to the floor.

4. The improvement of claim 1, including a plurality of said supports each positioned in the housing for supporting a separate representative sample of the charge of product, and a separate sensor operatively connected to each support.

5. The improvement of claim 2, wherein the proportioning means comprises a clamp pivotally attached to the load cell for receiving an end of the sample.

6. The improvement of claim 5, wherein the sensor is connected to the support at a first position, the proportioning means suspending the sample at a second position which is offset from the first position in the horizontal direction.

7. The improvement of claim 6, including adjusting means connected between the proportioning means and the sample for adjusting the second position for changing the resulting force being exerted by the weight of the sample on the sensor.

8. The improvement of claim 1, wherein the stand includes at least one leg at the lower end thereof and at least one fastener for fixing the leg to the floor.

9. The improvement of claim 1, wherein the stand is positioned between the charge and a wall of the kiln so the sensor is spaced both from the charge and from the wall.

10. The improvement of claim 8 wherein the leg extends substantially parallel to the floor, the floor having a blind bore therein and the fastener comprising a locator pin connected to the leg and extending downwardly into the blind bore.

11. The improvement of claim 10 including spacer means connected to the leg and engaged against the floor.

* * * * *